United States Patent [19]

Lanzone

[11] Patent Number: 5,709,465
[45] Date of Patent: Jan. 20, 1998

[54] DISPOSABLE SURGICAL LIGHT HANDLE COVER

[75] Inventor: Thomas S. Lanzone, Macedon, N.Y.

[73] Assignee: Getinge/Castle, Inc., Rochester, N.Y.

[21] Appl. No.: 568,634

[22] Filed: Dec. 7, 1995

[51] Int. Cl.[6] .............. F21L 15/00; F21L 15/12; B65D 65/00; B65D 65/02
[52] U.S. Cl. .............. 362/400; 362/399; 362/804
[58] Field of Search ............. 362/399, 400, 362/804; 16/111 R; 128/17; 428/343

[56] References Cited

U.S. PATENT DOCUMENTS

| 4,492,220 | 1/1985 | Hayes | 128/17 |
|---|---|---|---|
| 4,559,671 | 12/1985 | Andrews et al. | 16/111 R |
| 4,605,124 | 8/1986 | Sandel et al. | 362/399 |
| 4,722,296 | 2/1988 | Bowskill et al. | 362/804 |
| 4,795,669 | 1/1989 | Bowskill et al. | 362/804 |
| 4,807,600 | 2/1989 | Hayes | 128/17 |
| 4,844,252 | 7/1989 | Barron et al. | 362/804 |
| 4,974,288 | 12/1990 | Reasner | 362/804 |
| 4,975,826 | 12/1990 | Bell | 362/804 |
| 4,976,299 | 12/1990 | Bickelman | 362/804 |
| 5,036,446 | 7/1991 | Quintanilla et al. | 362/399 |
| 5,156,456 | 10/1992 | Hoftman et al. | 362/400 |
| 5,188,454 | 2/1993 | Quintanilla et al. | 362/399 |
| 5,355,292 | 10/1994 | Hoftman et al. | 362/400 |
| 5,469,600 | 11/1995 | Sandel | 362/399 |
| 5,534,346 | 7/1996 | Robinson | 428/343 |
| 5,599,093 | 2/1997 | Hoftman et al. | 362/804 |
| 5,604,955 | 2/1997 | Horan | 362/399 |

Primary Examiner—Ira S. Lazarus
Assistant Examiner—Matthew Spark
Attorney, Agent, or Firm—Trask, Britt & Rossa

[57] ABSTRACT

A disposable cover for a handle of a fixture which is normally positioned within a sterile field comprises first and second panels formed of flexible, medical grade plastic film material bonded together at portions of their respective perimeters to form a receptacle including an open cuff merging with a hollow sleeve which is closed except at the cuff and is shaped and dimensioned to receive a grip portion of the handle.

14 Claims, 4 Drawing Sheets

DISPOSABLE SURGICAL LIGHT HANDLE COVER

BACKGROUND

1. Field

This invention is directed to lighting systems used in operatory environments. It provides, among other things, a disposable prophylactic cover for the focusing handles of surgical lights.

2. State of the Art

A class of surgical lighting fixtures has evolved for use in situations requiring manipulation of a light head within a sterile field. It is not generally feasible to maintain the entire light head completely sterile during a procedure. Thus, if the light head is to be moved during a procedure, it must ordinarily be moved by non-sterile personnel who are not permitted to intrude into the sterile area. If sterile personnel come into contact with the non-sterile light head assembly, procedures must be followed to reestablish the required sterility. For example, it may be required for an attendant who has readjusted the positioning of the light head to re-glove after each such manipulation. Such procedures are time consuming and wasteful. They also present a substantial risk of inadvertent contamination.

Surgical lighting fixtures conventionally include handles which are utilized to steer and aim the lighting required in hospital operating rooms and other surgical settings; e.g., dental operatories. Removable sterilizable handles or disposable sterile handles have been used previously in connection with lighting fixtures used in operatories. Examples of such handles are disclosed by U.S. Design Pat. Nos. 279,611 and 289,206, for example, as well as by U.S. Pat. No. 4,844,252. Similar handles have been used in connection with x-ray tube head assemblies, as disclosed by U.S. Pat. No. 4,993,057.

Flexible protective coverings have long been used in medical environments. In some instances, these coverings are initially sterile. They may be disposable. U.S. Pat. Nos. 3,738,173 and 3,929,018, for example, disclose disposable covers for temperature sensing probes. U.S. Pat. Nos. 3,720,250 and 3,862,654 disclose protective covers for ampules. These structures offer protection against various forms of contamination or injury, but they have no application to preserving the sterility of the handles of operatory fixtures, such as surgical lighting systems.

U.S. Pat. No. 4,605,124 discloses a disposable cover for the handle of a surgical room light fixture. The cover is shaped and dimensioned to fit over a standard handle of approximately corresponding configuration. In that way, covers may be replaced as needed, provided the standard handle is in place. The covers do not fit reliably over the original handles of common surgical lighting arrangements. The standard handle is thus provided with a selection of adapters to facilitate its substitution for the original handles of various light fixtures present in the surgical rooms for which the disposable covers are vended. The cover itself has limited usefulness under circumstances in which the available light fixtures have not been retrofitted with the standard handles. U.S. Design Pat. No. 298,864 discloses a similar disposable cover. The illustrated design includes radial and annular reinforcing ribs which would interfere with flat storage configurations. The design of the '864 patent also appears to be adapted to a specific handle size and configuration.

There remains a need for a disposable cover for the original handles of surgical light fixture. Such a cover would avoid the inefficiencies and uncertainties associated with the need for retrofitting existing fixtures. The cover could also be used with the original handles of other assemblies requiring movement within a sterile field, such as an x-ray tube head assembly of the kind illustrated by the '057 patent.

SUMMARY OF THE INVENTION

According to this invention, a disposable cover is provided for a handle of a fixture which is normally positioned within a sterile field. Such handles typically include a handle grip portion extending from the fixture. The cover includes first and second panels, preferably formed of flexible, medical grade plastic film material. These panels are bonded together at portions of their respective perimeters to form a receptacle including an open cuff merging with a hollow sleeve, the sleeve being closed except at the cuff, and being shaped and dimensioned to receive the handle grip portion. The first and second panels are ideally cut from a pattern which fits within a square measuring approximately 9 inches on a side. A typical disposable cover of this invention comprises first and second approximately congruent panels, each of which is configured to have a relatively wide top portion merging into a relatively narrow cover grip portion. The panels are arranged in stacked relation, bonded together at their respective perimeters around the cover grip portion, and unbonded at the respective perimeters around at least a segment of the top portion, the first and second panels being rolled out away from each other at the top portion to form the cuff.

The disposable handle covers of this invention are constructed and arranged for direct usage with original handles of a wide variety of surgical or other operatory lights or devices. Ideally, the cover is soft in feel, with an inner smooth surface and an outer textured (or configurated) surface. It is generally prepackaged in sterile condition. Usually, one or more covers is provided within a sterile package, which may be opened in the operatory just prior to installation. Ideally, the covers are folded prior to packaging to reduce the size of the package. A plurality of pre-folded covers may be stacked flat within a heat sealed or blister pack package, for example. The thus-packaged covers may be sterilized in conventional fashion.

If a cover is folded within a package, it is unfolded upon removal from the package to a fully extended flat condition. In this condition, the cover comprises first and second, approximately congruent, flat panels. These first and second panels are bonded together around an appropriately configured perimeter, leaving an unbonded portion to serve as the open top of the cover. The first and second panels may be parted at the open top to form a hollow handle cover. This open cover may be slipped over the light head's original (or equivalent) handle. The security of the installation may be enhanced by firmly squeezing the cover upon the handle. According to certain preferred embodiments, adhesive is provided on a portion of the inner surface of the cover to assist in establishing a temporary bond at the interface between the cover and the handle.

The cover is configured and sized to fit essentially any of the handles normally encountered in the field. It is thus substantially universal in application without the need for retrofitting original light heads with the standard handle of a vendor.

The preferred embodiments are formed of durable, medical grade plastic film material, with a textured outer surface to facilitate non-slip gripping. The term "textured," within the context of this disclosure, refers to surface characteristics tending to increase the coefficient of friction of the surface, compared to a substantially smooth surface. Another preferred feature is the formation of a cup-shaped cuff portion at the open top of the cover incidental to its installation. This cuff portion functions to isolate a gloved hand from non-sterile surfaces. The first and second panels of the cover may be shaped to provide sufficient area of material at the open portion of their juxtaposed perimeters to permit the fashioning of a cuff by rolling the panels outwardly at the open top of the cover.

Use of the disposable covers of this invention avoids the downtime of operatory fixtures often required to replace contaminated handles or to re-glove. The current need for a hospital administrator to inventory expensive sterilizable, reusable handles is also avoided.

BRIEF DESCRIPTION OF THE DRAWINGS

In the drawings, which illustrate what is currently regarded as the best mode for carrying out the invention.

DESCRIPTION OF THE ILLUSTRATED EMBODIMENT

Figure 1:
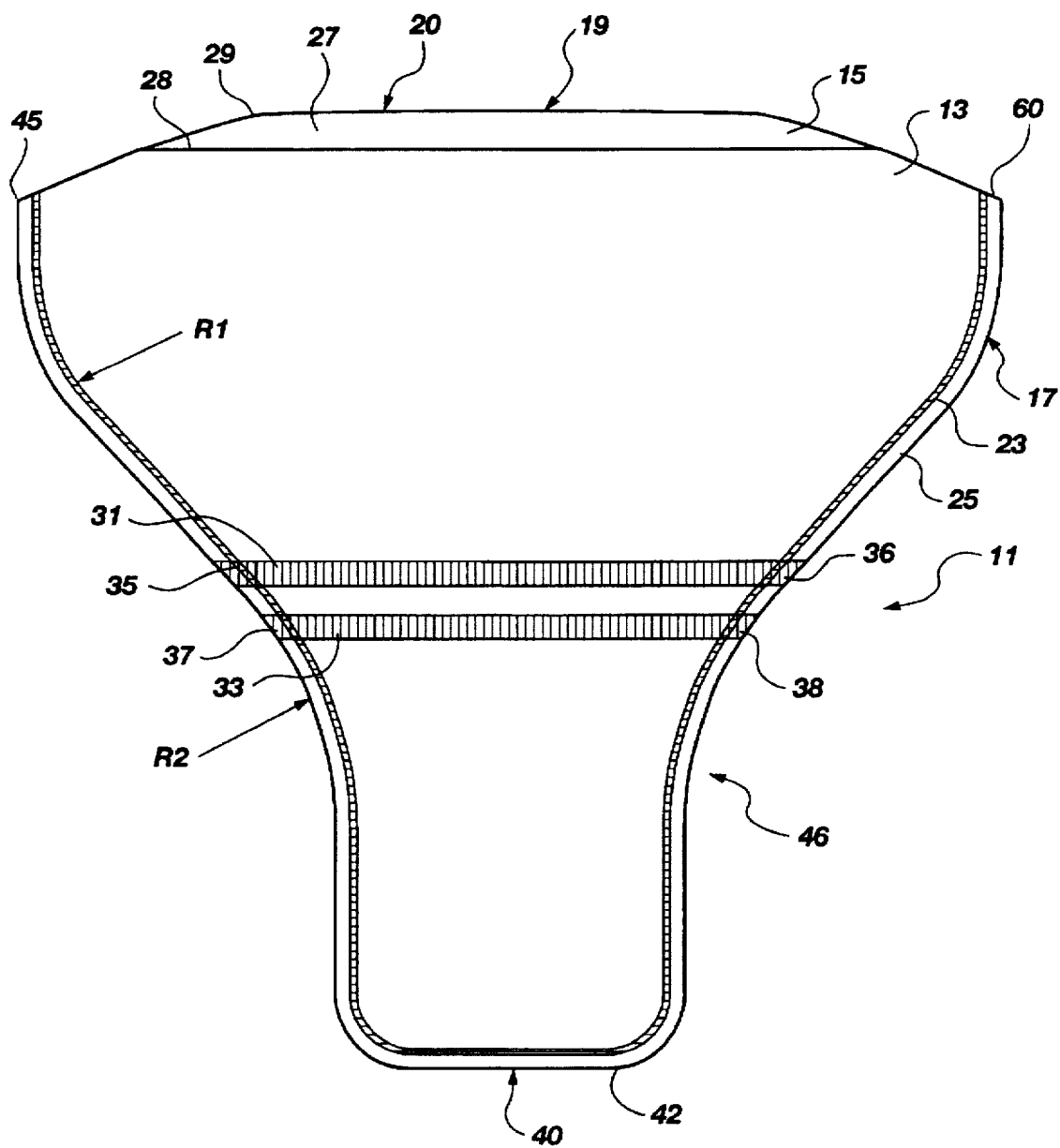
FIG. 1 is a plan view of a typical handle cover of this invention.

The handle cover, generally 11, illustrated by the drawings is constructed of a soft pliable thin medical grade polymeric film material. Virgin low density polyethylene film, nominally 0.002 inches thick, supplied by NAFCO CORP. is, a suitable material, although many other suitable medical grade materials having comparable engineering properties are commercially available. First (shown as front, or upper) 13 and second (shown as rear, or lower) 15 panels fashioned from this material are bonded, as by heat sealing, along the major portion of their common perimeter, generally 17, leaving an unbonded portion, generally 19, at the location regarded as the top, generally 20, of the cover 11. A satisfactory heat seal 23 is nominally 0.08 inches wide located approximately 0.12 inches inboard from the outer edge 25 of the panels 13, 15. The panels, 13, 15, are generally congruent, except that the lower panel 15 includes a tab portion 27 extending beyond the top edge 28 of the upper panel 13 to the top edge 29 of the lower panel 15.

First and second strips 31, 33 of adhesive are provided on the opposed inner surfaces of the panels 13, 15, at locations which avoid their mutual contact. As illustrated, the adhesive strips comprise lengths of 3M type 9424 removable tape, nominally 0.0055 inches thick and 0.25 inches wide. Opposite ends 35, 36, 37, 38 of the strips 31, 33 are shown included in the heat seal 23. The strips 31, 33 are anchored to the panels 13, 15 such that the high tack surface of strip 31 is oriented towards the smooth inner surface of the first panel 13 and the high tack surface of the strip 33 is oriented towards the smooth inner surface of the second panel 15. Because the inner surfaces of the panels 13, 15 are very smooth, there is little tendency for the adhesive strongly to adhere to those surfaces. Other embodiments locate the adhesive strips 31, 33 at approximately the same elevation. The adhesive is then selected to permit separation of the high tack surfaces of the strips without undue loss of the adhesion properties of these high tack surfaces.

In the exemplary case illustrated, the panels 13, 15 are cut from a pattern which fits within a square measuring less than approximately 9; e.g., 8.8 inches per side. The width of the tab 27 is approximately one third, e.g., 0.35 inch. The outside width of the bottom, generally 40, is approximately 3, e.g., 3.1 inches. Tape strip 31 is located approximately 4 and one-half; e.g., 4.4 inches above the bottom edge 42, and tape strip 33 is located approximately 4, e.g., 3.9 inches above that edge 42. The upper terminus 45 of the heat seal 23 is approximately 8 inches above the bottom edge 42. As illustrated, the radius of curvature R1 is approximately 2.25 inches, while the radius of curvature R2 is approximately 3.25 inches. In any case, the top portion 19 of the cover 11 merges into the cover grip portion, generally 46 through relatively gentle curvatures.

Figure 2:
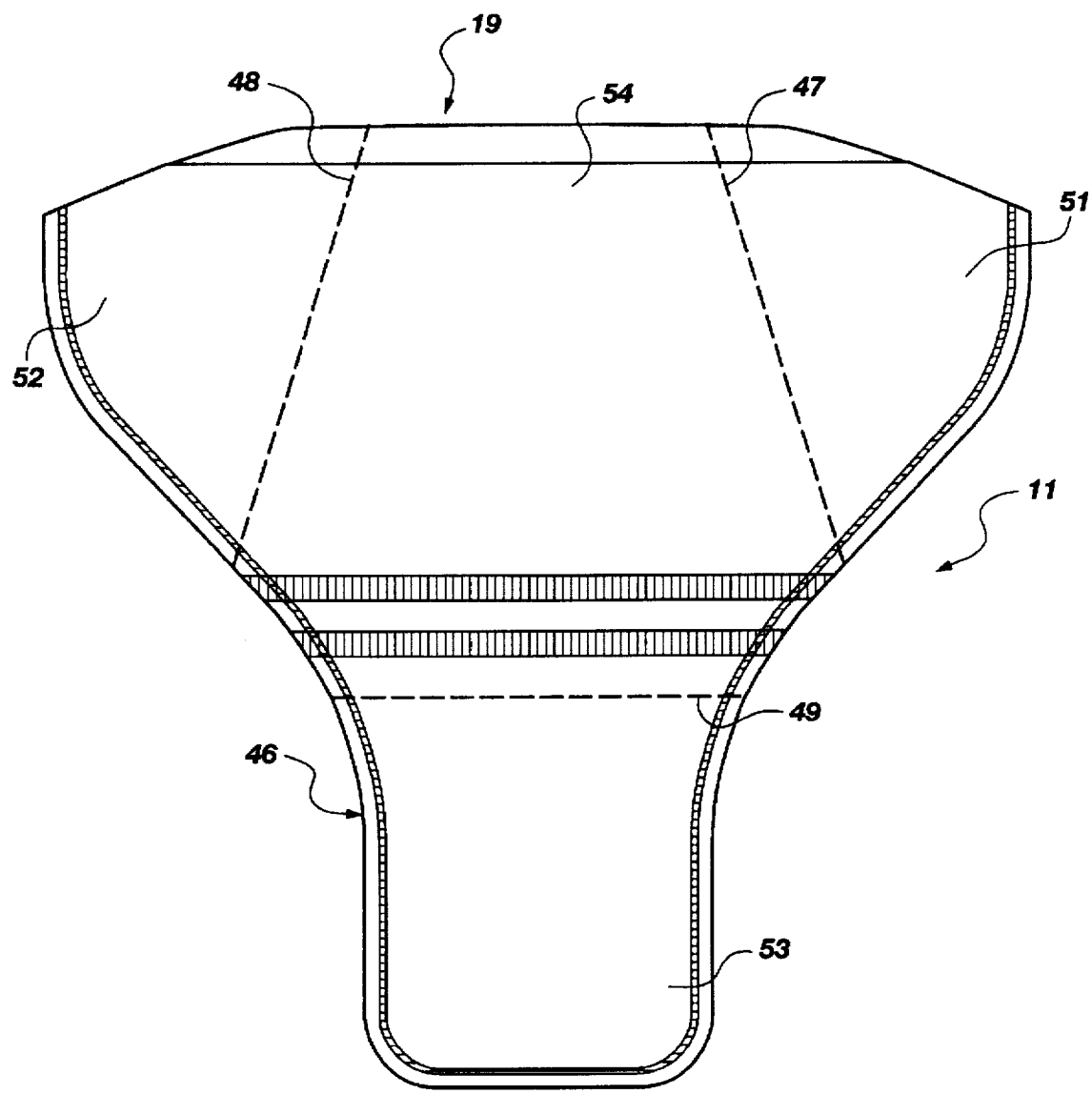
FIG. 2 is a view similar to FIG. 1, but showing fold lines.
Figure 3:
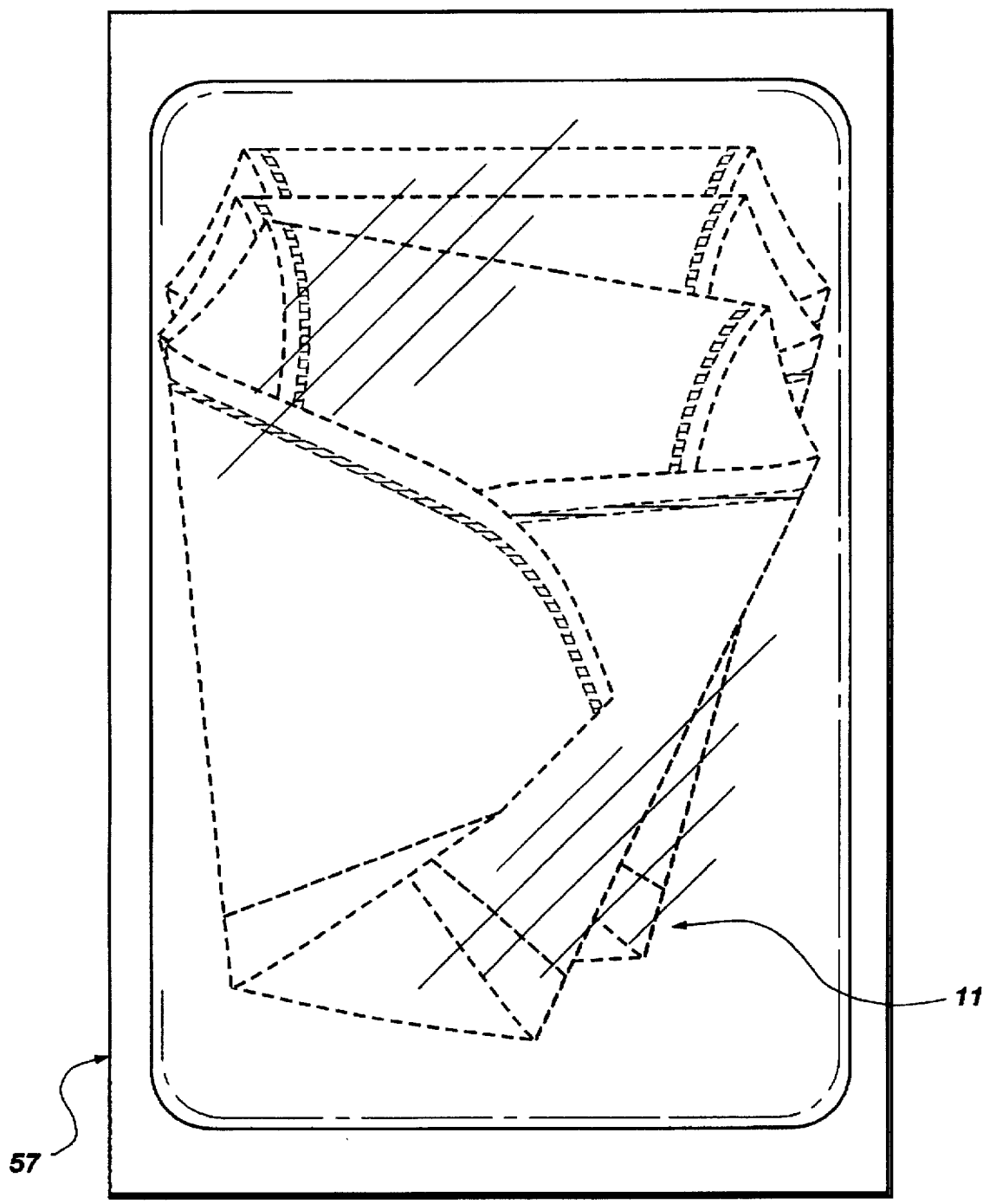
FIG. 3 is a pictorial view if the cover of FIG. 1 folded and stored within a sterile package.
Figure 4:
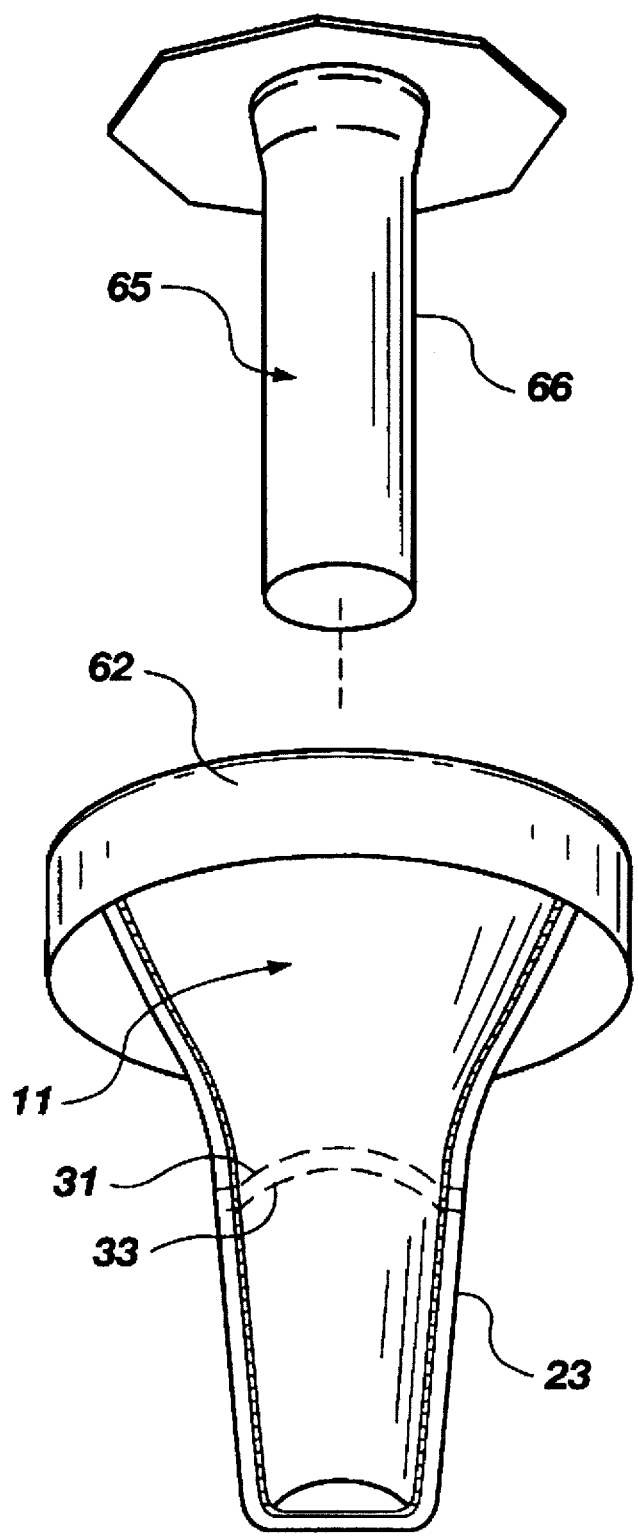
FIG. 4 is an exploded pictorial view of the cover of FIGS. 1 and 2 removed from its package and opened for installing on a typical surgical light handle.

FIG. 2 illustrates three fold lines, 47, 48, 49, about which the segments 51, 52, 53 may be rotated in sequence to stack upon the segment 54. The thus-folded cover 11 may then be individually packaged or a plurality of such folded covers may be stacked within a package, as illustrated by FIG. 3. In use, a disposable soft cover 11 of this invention is removed from its sterile package, generally 57, (or other suitable sterile storage environment, such as a sterile tray.) The cover 11 is arranged in an open flat condition, as shown by FIGS. 1 and 2. It may be opened for use by insertion of the thumbs of a user into the open top end 19, access being facilitated by the tab portion 27. The thumbs may be positioned adjacent the seam terminations 45, 60 (FIG. 1), and the seam 23 gripped at those locations with the thumbs inside and the finger tips outside the cover 11. It is then convenient to roll the top edges 28, 29 out and down over the finger tips to form a cuff 62, as best shown by FIG. 4. The strips 31, 33 may be separated by gentle finger pressure. The open cover may then be held in one hand and slid over a conventional surgical light handle, generally 65, as indicated by FIG. 4. The adhesive strips 31, 33 may be squeezed firmly against the exterior surface 66 of the handle 65 to assure adequate adhesion of the cover 11 to the handle 65 in its use position.

Reference in this disclosure to specific details of the illustrated or other preferred embodiments is not intended to limit the scope of the appended claims, which themselves recite those features regarded as important to the invention.

What is claimed is:

1. A disposable cover for a handle of a fixture which is normally positioned within a sterile field, said handle including a handle grip portion extending from said fixture, said cover comprising:

first and second, approximately congruent panels, each configured to have a relatively wide top portion merging into a relatively narrow cover grip portion, said panels being:

arranged in stacked relation, bonded together at their respective perimeters around said cover grip portion, unbonded at said respective perimeters around at least a segment of said top portion;

said first and second panels being formed from material having sufficient flexibility to permit said first and second panels to be rolled out away from each other at said top portion to form a cuff;

said cuff opening into a hollow sleeve having a volume sized and shaped to receive said handle grip portion.

2. A disposable cover according to claim 1, including adhesive located upon an inner surface of said hollow sleeve.

3. A disposable cover according to claim 1, wherein said first and second panels are cut from flexible film material.

4. A disposable cover according to claim 3, wherein said flexible film material comprises medical grade plastic.

5. A disposable cover according to claim 3, wherein said first and second panels are cut from a pattern which fits within a square measuring approximately 9 inches on a side.

6. A disposable cover according to claim 1, wherein each said panel comprises a smooth interior surface.

7. A disposable cover according to claim 6, wherein each said first and second panel comprises a textured outer surface.

8. A disposable cover for a handle of a fixture which is normally positioned within a sterile field, said handle including a handle grip portion extending from said fixture, said cover comprising:

first and second panels formed of flexible, medical grade plastic film material;

said panels being bonded together at portions of their respective perimeters to form a receptacle including an open cuff merging with a hollow sleeve, said sleeve being closed except at said cuff, and said sleeve being shaped and dimensioned to receive said handle grip portion.

9. A disposable cover according to claim 8, wherein each said first and second panel comprises a textured outer surface.

10. A disposable cover according to claim 8, wherein said first and second panels are cut from a pattern which fits within a square measuring approximately 9 inches on a side.

11. A disposable cover according to claim 8, including adhesive located upon an inner surface of said hollow sleeve.

12. A disposable cover according to claim 11, wherein each said first and second panel comprises a textured outer surface.

13. A disposable cover according to claim 12, wherein said first and second panels are cut from a pattern which fits within a square measuring approximately 9 inches on a side.

14. A disposable cover according to claim 13 wherein said first and second panels are approximately congruent, and each said panel is configured to have a relatively wide top portion merging into a relatively narrow cover grip portion, said panels being:

arranged in stacked relation;

bonded together at their respective perimeters around said cover grip portion; and unbonded at said respective perimeters around at least a segment of said top portion;

said first and second panels being rolled out away from each other at said top portion to form said cuff.

* * * * *